US007524283B1

(12) United States Patent
Johnstone, II

(10) Patent No.: US 7,524,283 B1
(45) Date of Patent: Apr. 28, 2009

(54) SEX TABLE

(76) Inventor: James R. Johnstone, II, 1407 Kinch St., Urbana, IL (US) 61802

( * ) Notice: Subject to any disclaimer, the term of this patent is extended or adjusted under 35 U.S.C. 154(b) by 688 days.

(21) Appl. No.: 11/215,541

(22) Filed: Aug. 30, 2005

Related U.S. Application Data

(60) Provisional application No. 60/607,213, filed on Sep. 2, 2004.

(51) Int. Cl.
*A61F 5/00* (2006.01)

(52) U.S. Cl. ........................................ 600/38; 128/845

(58) Field of Classification Search .................. 600/38; 128/845

See application file for complete search history.

(56) References Cited

U.S. PATENT DOCUMENTS

| | | | | |
|---|---|---|---|---|
| 2,659,365 | A | 11/1953 | Lewis | 601/60 |
| 2,694,394 | A | 11/1954 | Miller | 601/56 |
| 3,971,592 | A | 7/1976 | Farley | 297/448.2 |
| 4,055,170 | A | 10/1977 | Nohmura | 601/47 |
| 4,571,761 | A | 2/1986 | Perlin | 5/652 |
| 4,722,327 | A | 2/1988 | Harvey | 601/97 |
| 4,790,296 | A | 12/1988 | Segal | 601/97 |
| 5,076,261 | A | 12/1991 | Black | 601/93 |
| 5,385,154 | A | 1/1995 | Fuhrman et al. | 128/845 |
| 5,443,532 | A | 8/1995 | Hudak | 5/652 |
| 5,453,080 | A | 9/1995 | Mitchum, Jr. | 600/38 |
| 5,875,779 | A | 3/1999 | Fuhrman et al. | 128/845 |
| 6,135,552 | A | 10/2000 | Waguri | 297/245 |
| 6,199,552 | B1 * | 3/2001 | Crespo | 128/845 |
| 6,640,808 | B1 | 11/2003 | Fessler | 128/845 |
| 2003/0111876 | A1 * | 6/2003 | Black | 297/179 |
| 2005/0272970 | A1 * | 12/2005 | Lee | 600/38 |
| 2006/0004251 | A1 * | 1/2006 | Bookwalter et al. | 600/38 |

* cited by examiner

*Primary Examiner*—John P Lacyk
(74) *Attorney, Agent, or Firm*—Philip L. Bateman

(57) ABSTRACT

This invention relates to a machine consisting of a fixed base and a reciprocating platform which imparts that reciprocating motion to a person lying, kneeling, or sitting upon it. A gear motor mounted in the base of the machine drives an eccentrically mounted cam roller. As the cam roller rotates, it is retained in a channel on the underside of the reciprocating platform. The eccentric rotation of the cam roller is converted to linear motion, causing the platform to move back and forth on rollers. The reciprocating motion has a stroke of about one to six inches and a frequency of about 10 to 200 cycles per minute. A detachable appliance mounting holder allows the user to mount a dildo of their choosing to the fixed base in genital proximity. The reciprocating motion of the platform is an aid to sex for both healthy and physically challenged individuals when used with another person for partner sex or used with a dildo for solo sex.

18 Claims, 7 Drawing Sheets

SEX TABLE

CROSS-REFERENCE TO RELATED APPLICATION

This application claims the benefit of U.S. Provisional Application Ser. No. 60/607,213, Sep. 2, 2004.

FIELD OF THE INVENTION

This invention relates to sex machines. More particularly, this invention relates to sex machines that provide movement to a person during sex.

BACKGROUND OF THE INVENTION

Humans reproduce by sexual intercourse in which a man's erect penis is moved in a reciprocating motion inside a woman's vagina. While all higher form animals reproduce by sexual intercourse, humans differ from other animals in many aspects of sex. First, humans engage in sex for reasons other than reproduction, including physical and emotional pleasure. Second, humans perform sexual intercourse in countless different positions. Third, in addition to vaginal sex, humans also perform oral sex and anal sex. Sex in which a bodily orifice is penetrated by a penis or a tongue is referred to herein as partner sex.

A variety of products are used by humans to enhance sex. One of the most popular sex enhancement products are dildos. Dildos have the general shape and size of an erect penis. They are made of a variety of materials and some include vibrating motors. Dildos enable a person to enjoy penetration without a partner. Sex in which a bodily orifice is penetrated by a dildo is referred to herein as solo sex. Dildos are generally held in the hand during penetration, but they are sometimes held in the mouth, mounted on a harness worn by a person, mounted on a holder, or placed against another surface.

Another type of sex enhancement products are machines that provide movement to one or both of the sexual partners. One class of machines are beds, benches, and stools that provide vibrations to the occupant. For example, Lewis, U.S. Pat. No. 2,659,365, issued Nov. 17, 1953, discloses a vibratory apparatus which is attached to a bed or to a bridge structure that rests on top of a bed to provide massage therapy. Miller, U.S. Pat. No. 2,694,394, issued Nov. 16, 1954, disclosed a bench-like seat with a vibratory element attached to the underside of the seat. Nohmura, U.S. Pat. No. 4,055,170 issued Oct. 25, 1977, discloses a health promoting apparatus consisting of a chair with a built in loudspeaker, which allows sound waves to be transmitted to the body of the person seated in it. All of these machines utilize a vibratory element to deliver energy to the user. This vibratory energy is typically at a frequency at, or above, 60 cycles per second (line frequency of household electrical current) and is generated by a solenoid or by a motor with an eccentrically weighted shaft or, in one case, by sound waves. The physical displacement of the body of the user, resulting from the vibratory energy imparted by these inventions, would typically be very small and localized (perhaps less than 0.1 inch).

A second class of machines are penetration devices for use in solo sex, i.e., by a single person. The majority utilize a dildo which is moved by a drive mechanism in a reciprocating fashion. For example, Harvey, U.S. Pat. No. 4,722,327, issued Feb. 2, 1988, discloses a machine having a dildo that extends from a drive housing that is driven in a reciprocating motion along tracks on a platform base. Segal, U.S. Pat. No. 4,790,296, issued Dec. 13, 1988, discloses a similar machine consisting of an attachment device which extends from a drive housing. This invention allows the user to attach a dildo (or a simulated female vagina) which is driven in a reciprocating motion. Black, U.S. Pat. No. 5,076,261, issued Dec. 31, 1991, likewise discloses a machine that has a dildo that extends from a drive housing. However, this drive mechanism introduces a random element to the motion due to the internal mechanism being suspended by elastic bands rather than a rigid motor mount. The user typically lies or kneels in close proximity to these machines and the dildo is driven into and out of one of the bodily orifices. These machines must be positioned by the user on a suitable surface such as a bed or the floor and there are no provisions for easily adjusting the machines for users of different heights in different positions. In addition, these machines are relatively light weight and do not provide the thrusting force of a full sized, adult partner.

A variety of machines have also been developed for the purpose of assisting couples with the physical aspects of sexual activity. For example, Farley, U.S. Pat. No. 3,971,592 issued Jul. 27, 1976, discloses a chair with a cutout in the seat for aiding sex for the infirm. Perlin, U.S. Pat. No. 4,571,761 issued Feb. 25, 1986 discloses a cutaway bed or lounge which allows a man to lie on his back while the woman stands over him with her legs in the cut out areas of the horizontal surface. Fuhrman et al., U.S. Pat. No. 5,385,154 issued Jan. 31, 1995 discloses a machine consisting of two seats facing one another on a horizontal track and a means of moving at least one of the seats toward and away from the other in a longitudinal direction for the purpose of reducing the effects of gravity and the expenditure of energy during sex. Hudak, U.S. Pat. No. 5,443,532 issued Aug. 22, 1995 discloses an inclined table with handles and stirrups for the purpose of enhancing sex.

Mitchum, Jr. U.S. Pat. No. 5,453,080 issued Sep. 26, 1995, discloses a machine similar to the aforementioned Fuhrman machine in which a disabled person is seated and their upper body supported while their partner is seated facing them. A hand lever or electric motor allows the partner's seat to be driven toward and away from the fixed seat of the disabled user. Fuhrman et al., U.S. Pat. No. 5,875,779 issued Mar. 2, 1999, discloses an arcuately reciprocating human sexual fitness machine. It too consists of two seats facing one another. Both are on rollers on a horizontal track, at floor level, to facilitate movement toward and away from one another. Waguri, U.S. Pat. No. 6,135,552 issued Oct. 24, 2000 discloses a rocking chair device for the purpose of assisting sexual intercourse of old or handicapped persons. It consists of two facing seats that are rocked toward and away from one another by an electric motor which, is tied to the seats by an eccentrically operated linkage. Fessler U.S. Pat. No. 6,640,808 issued Nov. 4, 2003, discloses an apparatus for sexual intercourse which consists of a flat padded support suspended by springs from a large frame. The frame incorporates foot rests and a handrail to accommodate a variety of sexual positions.

Most of the aforementioned inventions rely on human power or the use of springs or elastic cords to facilitate movement. All have limited or no adjustability to accommodate the physical differences from one person to the next. Accordingly, there exists a demand for a machine that incorporates the elements of a large displacement, moving or reciprocating platform with a penetration device. Further, a demand exists for a machine that is adjustable to accommodate users of varying statures and flexible enough to be used either with two persons in partner sex or by a single person in solo sex.

SUMMARY OF THE INVENTION

The general object of this invention is to provide an improved sex machine. A more particular object is to provide a reciprocating sex table upon which a person lies that can be used for partner sex or solo sex.

I have invented an improved sex table. The table comprises: (a) a base; (b) a platform mounted on the base, the platform being adapted for supporting a user at a height of about one to three feet; and (c) a means for moving the platform in a reciprocating motion relative to the base, wherein the reciprocating motion has a stroke of about one to six inches and a frequency of about 10 to 200 cycles per minute.

The sex table enables a user to enjoy the reciprocating penetration by a partner's erect penis without the need for the user or partner to move.

DETAILED DESCRIPTION OF THE INVENTION

Figure 1:
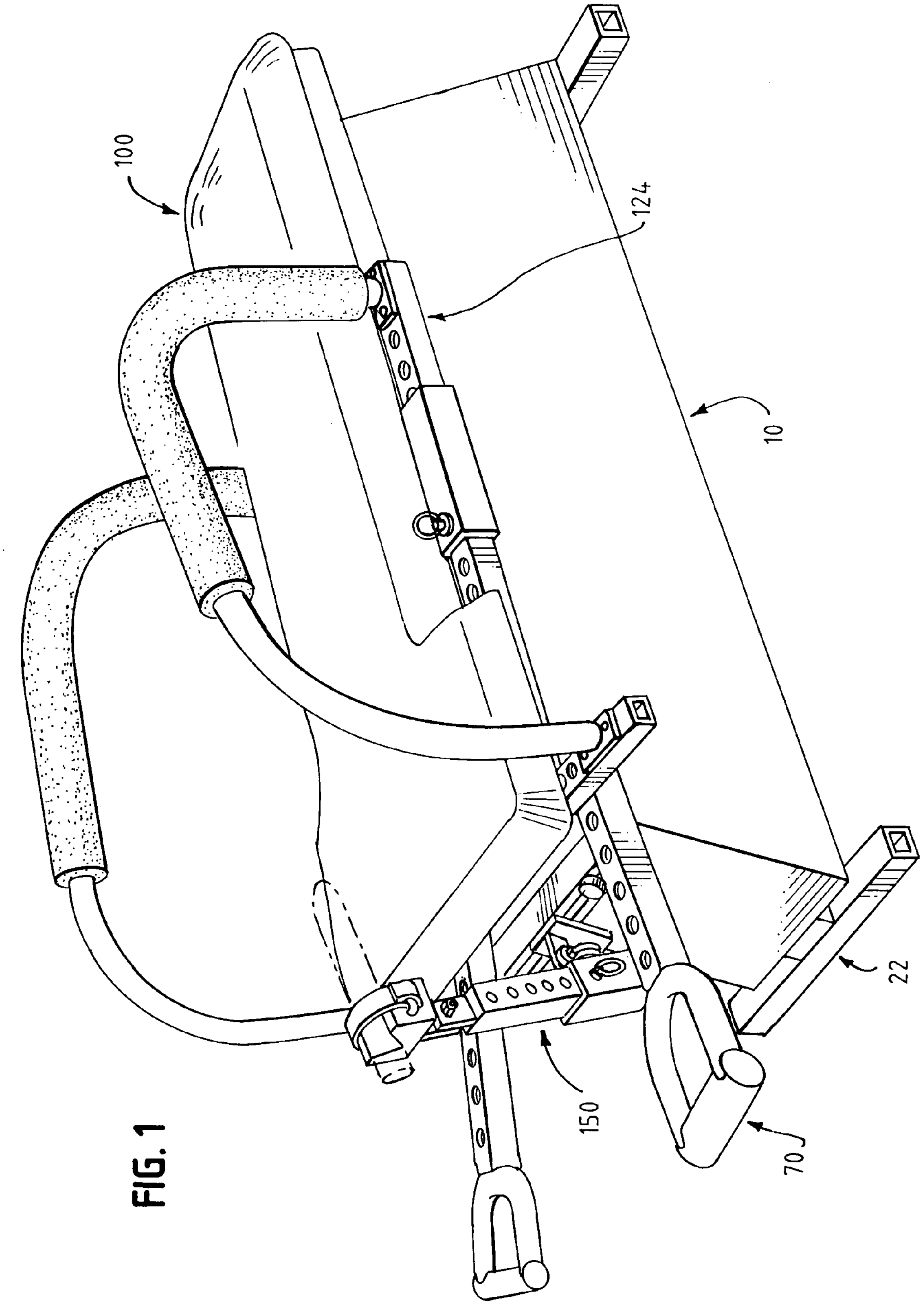
FIG. 1 is a perspective view of one embodiment of the reciprocating sex table machine of this invention.

The sex table of this invention enables the user to lie, sit, or kneel upon a reciprocating platform in a comfortable position. The user controls the speed at which the platform reciprocates by means of a speed control such as a rheostat or the like. The user may wish for the platform to reciprocate in a slow, gentle, rocking motion or in a more aggressive thrusting motion. The sex table can be used in two basic ways. The first way is for partner sex with a partner standing at the foot end of the machine maintaining genital penetration. The second way is for solo sex. The sex table preferably incorporates a detachable appliance mounting holder for the purpose of positioning a dildo in a manner that facilitates vaginal or anal penetration when the user is lying, sitting, or kneeling on the reciprocating platform.

The sex table comprises a moveable platform mounted on rollers on top of a fixed base. Also mounted on the underside of the platform is a transverse channel or pocket. A gear motor is mounted on the base of the machine to drive the reciprocating movement of the platform. Output RPM (revolutions per minute) of the gear motor can be fixed or variable but would typically be in the range of about 10 to 200 rpm, preferably about 50 to 100 rpm. A cam roller (a shaft mounted bearing designed to follow an internal or external cam surface) is mounted to the output shaft of the gear motor by means of an eccentric coupling and drives the platform longitudinally, back and forth, as it rotates in an eccentric fashion in the transverse channel on the underside of the platform. The eccentricity of the coupling would typically be in the range of about one-half to three inches, preferably about one to two inches, and relates to the stroke, or displacement, of the platform by the formula:

$$\text{Stroke} = 2 \times \text{Eccentricity}$$

Thus, an eccentricity of one-half inch yields a stroke of one inch and an eccentricity of three inches yields a stroke of six inches. The rotational motion of the motor and cam roller are converted to linear motion of the platform and the RPM of the motor relates directly to the frequency of the platform reciprocation (100 RPM motor speed yields 100 cycles per minute of platform reciprocation). Accordingly, the platform typically reciprocates at about 10 to 200 cycles per minute, preferably about 50 to 100 cycles per minute.

Unlike the prior art, this design drives the entire body of the user back and forth in a reciprocating motion with considerable force and displacement. This motion may be utilized as a massage therapy to reduce tension and stress by rocking the user in a back and forth motion. The motion may also be utilized in a plurality of ways as an aid to sexual activity for either healthy or physically challenged individuals. The machine drives the body of the user in a reciprocating motion so that the only action required by a sexual partner is to stand at the end of the machine and maintain genital penetration while the machine does the work. The reciprocating motion can also improve the effect of oral stimulation by a partner on the user by adding a thrusting component to the activity that would not normally be possible with oral sex. The design also incorporates a detachable appliance holder mounted on the fixed base which allows the user to self stimulate using a dildo. The appliance is adjusted for penetration when the user's body is thrust back and forth in the reciprocating motion.

Physically challenged individuals may also benefit from this design because they sometimes lack the strength or endurance to engage in sexual activity in the traditional manner. This design allows them to participate in the experience by reducing the physical strength and exertion required to engage in sexual activity. In addition, the flexibility of the design facilitates stimulation either alone or with a partner. Other features and advantages of the present invention will become apparent from the following more detailed description taken in conjunction with the accompanying drawings which illustrate the principles of the invention.

Referring now to the drawings, FIG. 1 illustrates a perspective view of the sex table 10 of the present invention along with the leg assembly 22, the stirrup assembly 70, the reciprocating platform 100, the shoulder tube assembly 124, and the appliance mounting assembly 150.

Figure 2:
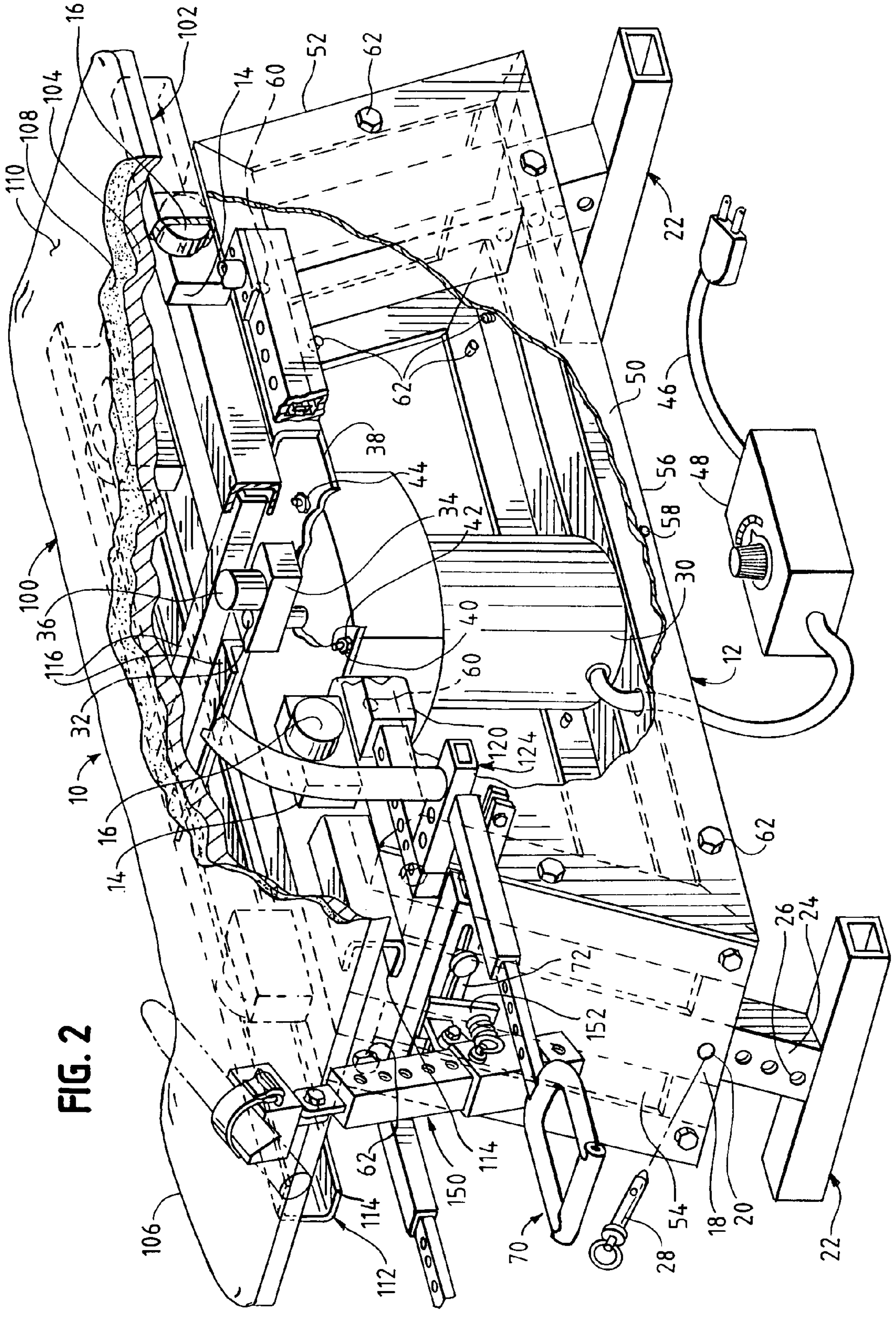
FIG. 2 is a cut away perspective view thereof.

In FIG. 2, greater detail of the sex table is shown in cut away. The sex table features a fabricated steel lower frame 12 to which the parallel shaft gear motor 30 is mounted by means of a motor mounting plate 38 welded to the lower frame. The motor mounting studs 40 on the gear motor fit through the mounting holes 42 and are secured by nuts 44 thus fixing the gear motor to the motor mounting plate. Attached to the output shaft 32 of the gear motor is an eccentric coupling 34 consisting of a block with two, side by side bores. The gear motor fits into the smooth bore and the drive cam roller 36 screws into the second bore on the eccentric coupling. The gear motor is powered by household electrical current via a power cord 46. The speed of the gear motor can be controlled by means of a rheostat 48 or the like.

The lower frame is enclosed for both safety and cosmetic reasons. Two side panels 50 enclose the sides of the lower frame. Two panels enclose the ends of the machine, the end panel foot 54 and the end panel head 52. A bottom panel 56 completes the enclosure. Each of the side panels, end panel foot, end panel head, and bottom panel have through holes 58 along the perimeter of the panels for attachment to threaded holes 60 in the lower frame by means of a standard bolt 62.

The lower frame has a down tube 18 at each end which serves as the outer section of the telescoping height adjustment for the sex table. Each down tube has a single through hole 20 at the bottom end. Sliding inside each down tube is a leg assembly 22. The leg assembly is shaped like an inverted "T". The vertical tube 24 of the leg assembly consists of a square tube, the outside dimensions of which are slightly smaller than the inside dimensions of the down tube, allowing the vertical tube of the leg assembly to slide (telescope) into and out of the down tube. Additionally, the vertical tube has holes 26 spaced along the length of the tube at intervals of approximately one inch. The height of the sex table is adjusted in a manner similar to that of an automotive jack stand and the like by supporting the weight of the platform with one hand and adjusting (sliding) the position of the leg assembly to the desired height. When a hole in the vertical tube 24 of the leg assembly lines up with the single through hole in the down tube, the user inserts a pin 28 to fix the height of the sex table. Since the adjustment of the height of the sex table is independent on each end, the height may be adjusted evenly for operation in a horizontal plane or unevenly to position the body of the user in an inclined configuration, either head up or head down, as the user desires.

FIG. 2 shows the general location of the stirrup assembly 70 on the sex table. The stirrup assembly is adjustable to support the legs and feet of the user in various positions and is attached to the lower frame by means of the cross tube outer 72. The cross tube outer is a square tube and is welded to the lower frame.

Figure 5:
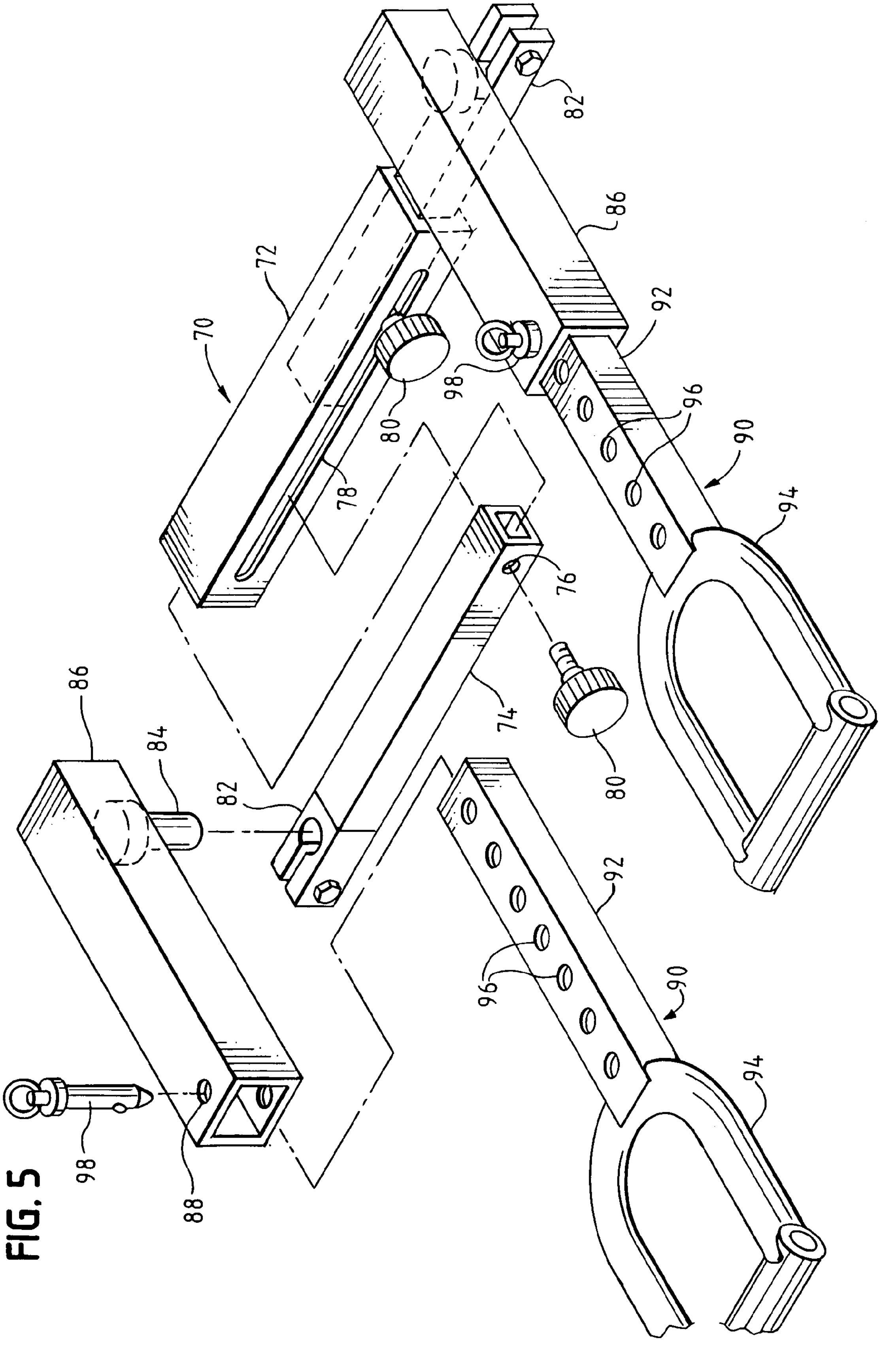
FIG. 5 is an exploded perspective view of the stirrup assembly.

Referring to FIG. 5 for greater detail, the cross tube inner 74 consists of a square tube, the outside dimensions of which are slightly smaller than the inside dimensions of the cross tube outer. The cross tube inner has a threaded hole 76 in the side wall of the tube that aligns with a slotted hole 78 in the cross tube outer. The lateral position of the cross tube inner can be adjusted with respect to the cross tube outer to control the spread of the users legs by loosening a clamping bolt 80 and sliding the cross tube inner into or out of the cross tube outer and re-tightening the clamping bolt. One cross tube inner slides into each end of the cross tube outer. On the outboard end of each cross tube inner is a pinch clamp 82. A stub shaft 84 is inserted into the pinch clamp and allows for angular adjustment of the stirrup tube outer 86 to which the stub shaft is attached. On the end opposite the stub shaft on the stirrup tube outer is a single through hole 88. The stirrup tube assembly 90 consists of the stirrup tube inner 92 and the stirrup 94. The stirrup tube inner is a square tube with holes 96 spaced longitudinally along the length of the tube at intervals of approximately one inch and the outside dimensions of which are slightly smaller than the inside dimensions of the stirrup tube outer. The stirrup tube inner portion of the stirrup tube assembly slides into the stirrup tube outer and the position can be fixed by aligning one of the holes in the stirrup tube inner with the single through hole in the stirrup tube outer and inserting a pin 98.

Referring once again to FIG. 2, affixed to the center of the cross tube outer is the appliance mounting assembly 150 which provides the user with a method of mounting a dildo to the lower frame for solo sex. A base plate 152 of the appliance mounting assembly is welded in a generally central location in the transverse direction on the cross tube outer.

Figure 7:
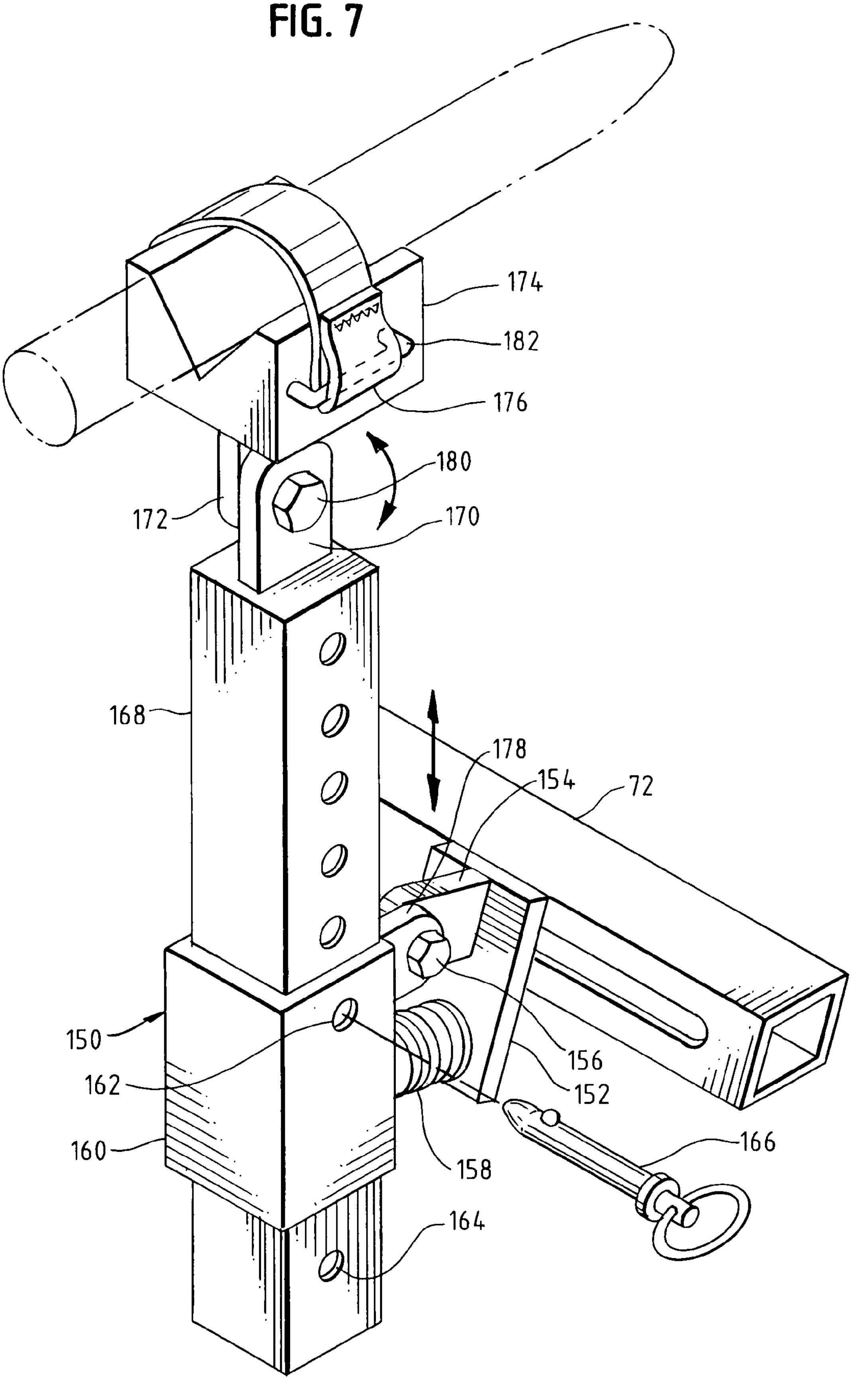
FIG. 7 is a perspective view of the appliance mounting assembly.

Referring to FIG. 7 for greater detail, a base pivot tab 154 on the base plate mates to a tube outer tab 178 on the appliance mounting tube outer 160 by means of a shoulder bolt 156. A spring 158 centers the appliance mounting tube outer with respect to the base plate and helps absorb the shock of the users body being pushed up against the appliance in the appliance mounting assembly by pivoting the appliance mounting tube outer around the shoulder bolt, thus preventing injury to the user. The appliance mounting tube inner 168 is a square tube with holes 164 spaced along the length of the tube at intervals of approximately one inch and the outside dimensions of which are slightly smaller than the inside dimensions of the appliance mounting tube outer. The height of the appliance mounting assembly is adjusted by sliding the appliance mounting tube inner inside the appliance tube mounting outer and lining up the desired hole in the appliance mounting tube inner with the single through hole in the appliance mounting tube outer and inserting a pin 166.

On the upper end of the appliance mounting tube inner is a pivot tab tube inner 170 which mates to the pivot tab mounting block 172. The joint is clamped by a bolt 180 when the user has adjusted the mounting block 174 to the desired angle. The mounting block is a "V" block configuration molded or cut from a resilient material such as urethane or the like and shaped as such for the purpose of centering a generally round appliance within a range of diameters. Affixed to each side of the mounting block is a "D" ring 182 which provides an attachment point for each end of the hold down strap 176. The hold down strap is fabricated from either an elastomer such as rubber, or a webbed fabric of sufficient tensile strength to adequately clamp an appliance in the mounting block without breaking or allowing the appliance to slide longitudinally in the mounting block. The appliance mounting tube inner may be removed from the appliance mounting assembly to eliminate that portion of the assembly as an obstacle to the performance of normal sexual activity with a partner standing at that end of the sex table.

Figure 3:
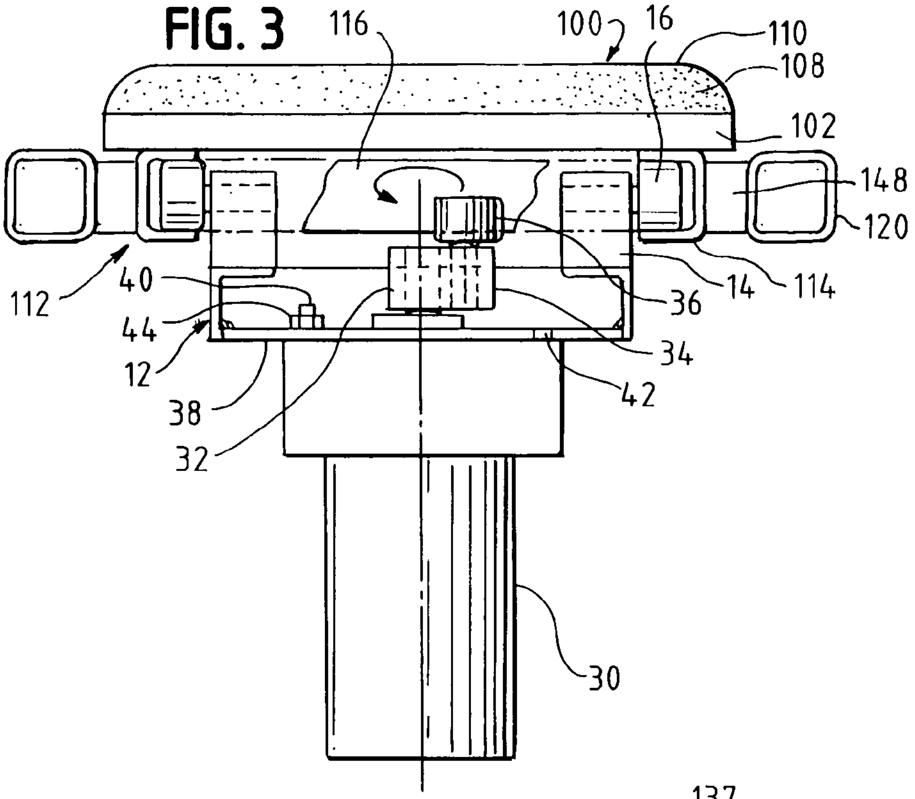
FIG. 3 is a cut away end elevation view thereof.
Figure 6:
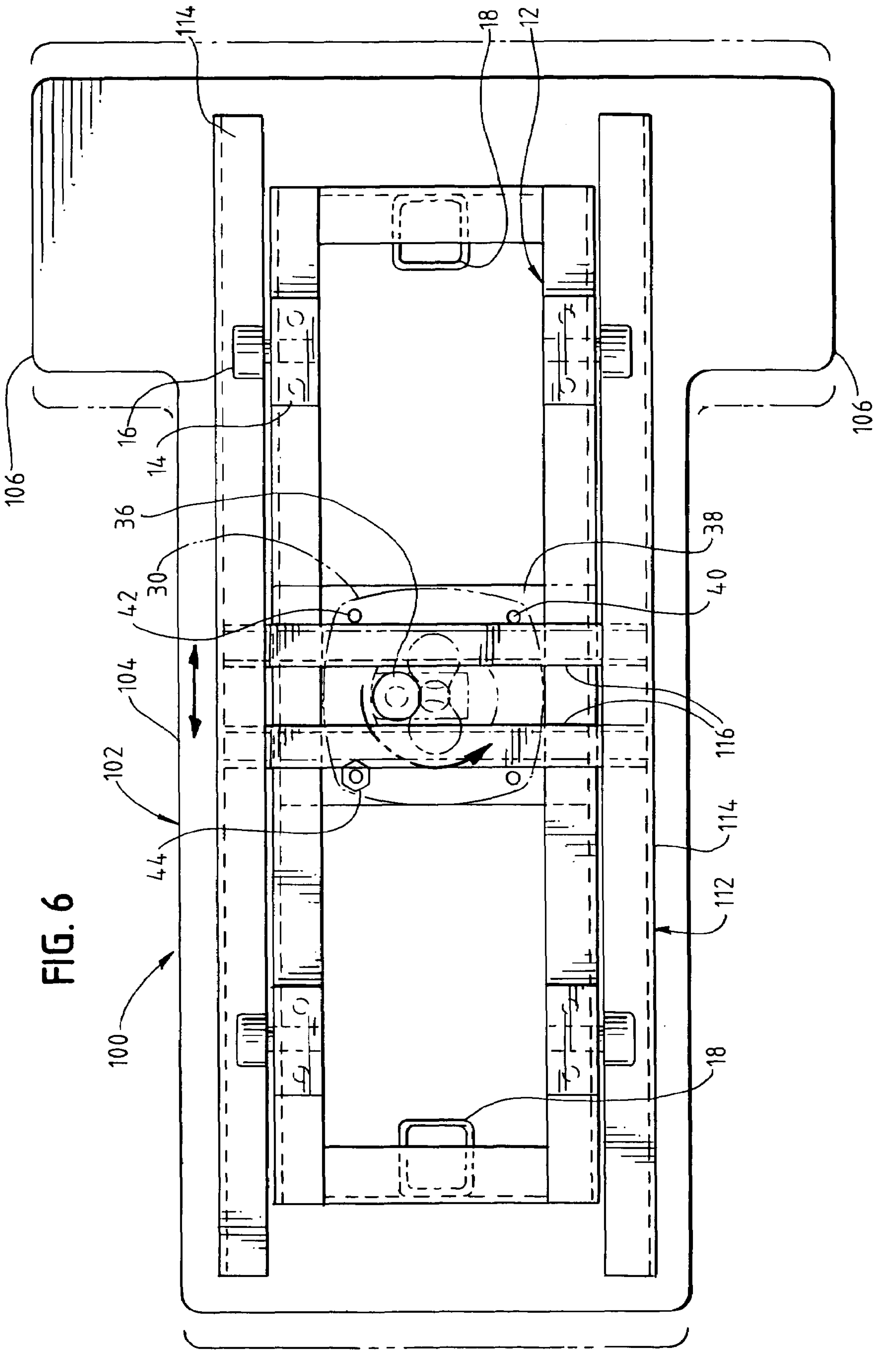
FIG. 6 is a plan view of the reciprocating machine.

Referring back to FIG. 2, also attached to the lower frame are four mounting blocks 14 for the cam rollers 16 that support the reciprocating platform assembly 100. FIGS. 3 and 6 represent end elevation and plan views, respectively, of the sex table and supplement FIG. 2 in facilitating an understanding of the means by which the reciprocating motion is generated. The reciprocating platform assembly comprises a fabricated steel upper frame 112. The upper frame consists of channel shaped side rails 114 where the afore mentioned cam rollers 16 support the reciprocating platform assembly as well as two transverse angle members 116 which form the channel where the drive cam roller 36 is captive and the longitudinal component of the eccentric motion of which generates the reciprocating motion of the platform assembly. The channel shaped side rails hold the reciprocating platform assembly captive on the cam rollers so that the reciprocating platform assembly does not separate from the lower frame during operation.

Figure 4:
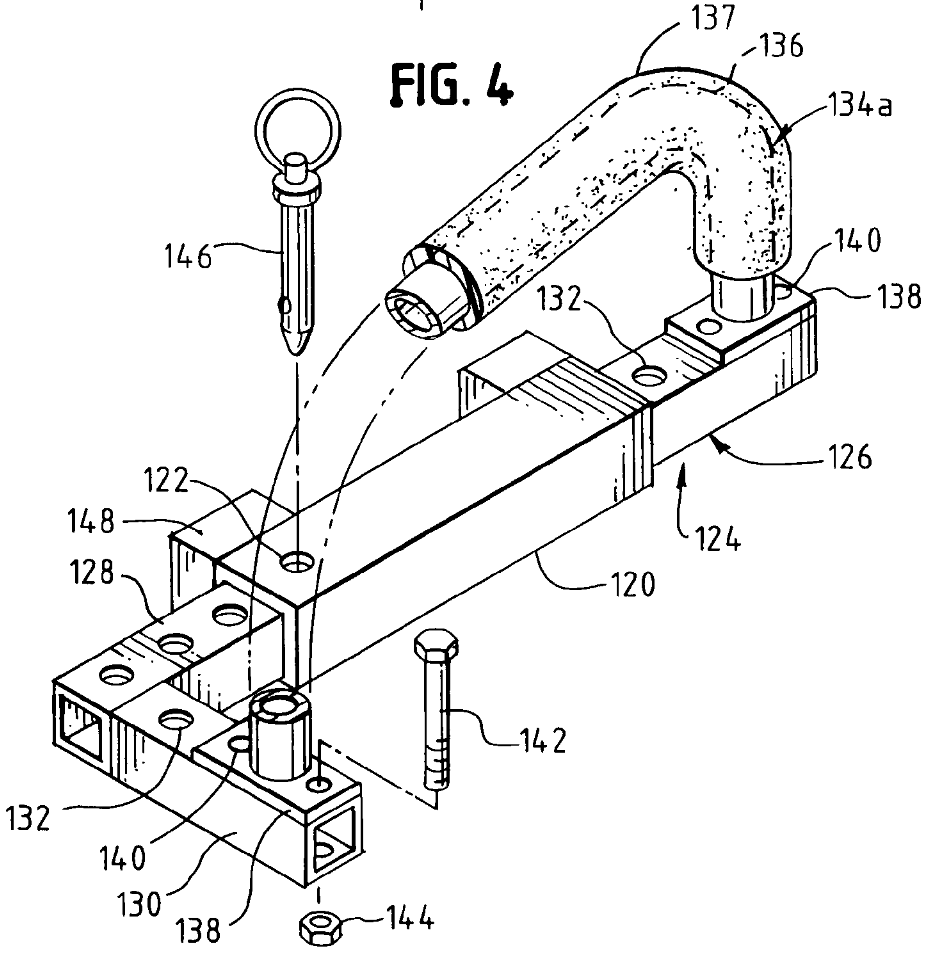
FIG. 4 is a perspective view of the shoulder tube assembly.

Referring back to FIG. 2, attached to the outboard side of each channel shaped side rail is the shoulder tube outer 120. FIG. 4 shows in detail that the shoulder tube outer consists of a square tube with a single through hole 122 in one end and spacer blocks 148 affixed to the inboard side. The spacer blocks are used to position the shoulder tube outer such that the shoulder tube assembly 124 has clearance with the platform board 102. The shoulder tube assembly consists of the shoulder tube inner assembly 126 comprised of the shoulder tube inner 128 and the offset tube 130. The shoulder tube inner is a square tube with holes 132 spaced longitudinally along the length of the tube at intervals of approximately one inch and outside dimensions of which are slightly smaller than the inside dimensions of the shoulder tube outer. The longitudinal position of the shoulder tube assembly is adjustable for users of varying stature by sliding the shoulder tube assembly to the desired position within the shoulder tube outer, lining up the single through hole with the desired hole in the shoulder tube inner, and inserting the pin 146. The offset tube is welded to the shoulder tube inner at right angles and also has holes 132 spaced longitudinally along the length of the tube on approximately one inch centers.

The upper portion of the shoulder tube assembly 124 consists of the shoulder tube assembly upper 134. The shoulder tube assembly upper is comprised of an inverted "U" shaped shoulder tube 136 with mounting flanges 138 on each end. The shoulder tube is covered with shoulder tube padding 137 to cushion the user's shoulders from the acceleration forces generated by the reciprocating sex table. The left and right sides of the shoulder tube upper are symmetrically opposite and are designated as shoulder tube upper left 134*a* and shoulder tube upper right 134*b*. Each mounting flange has two holes 140 for attaching the shoulder tube assembly upper to the shoulder tube inner assembly by lining up the holes 140 in the mounting flange with the holes 132 in the shoulder tube inner and the offset tube and inserting a conventional bolt 142 and nut 144.

FIG. 3 shows that a foam rubber pad 108 is placed on top of the platform for user comfort and the foam rubber pad is upholstered with a vinyl or leather top cover 110. FIG. 6 shows that the platform is shaped like a "T". The stem of the "T" is the back board 104 portion of the platform. The back board supports the user when lying on the sex table with the head of the user toward the bottom of the stem of the "T" and the hips of the user resting on the crossed part of the "T". The crossed part of the "T" is also the knee wings 106 portion of the platform. The knee wings are wider than the back board and support the user kneeling or sitting on the reciprocating platform.

Figure 8:
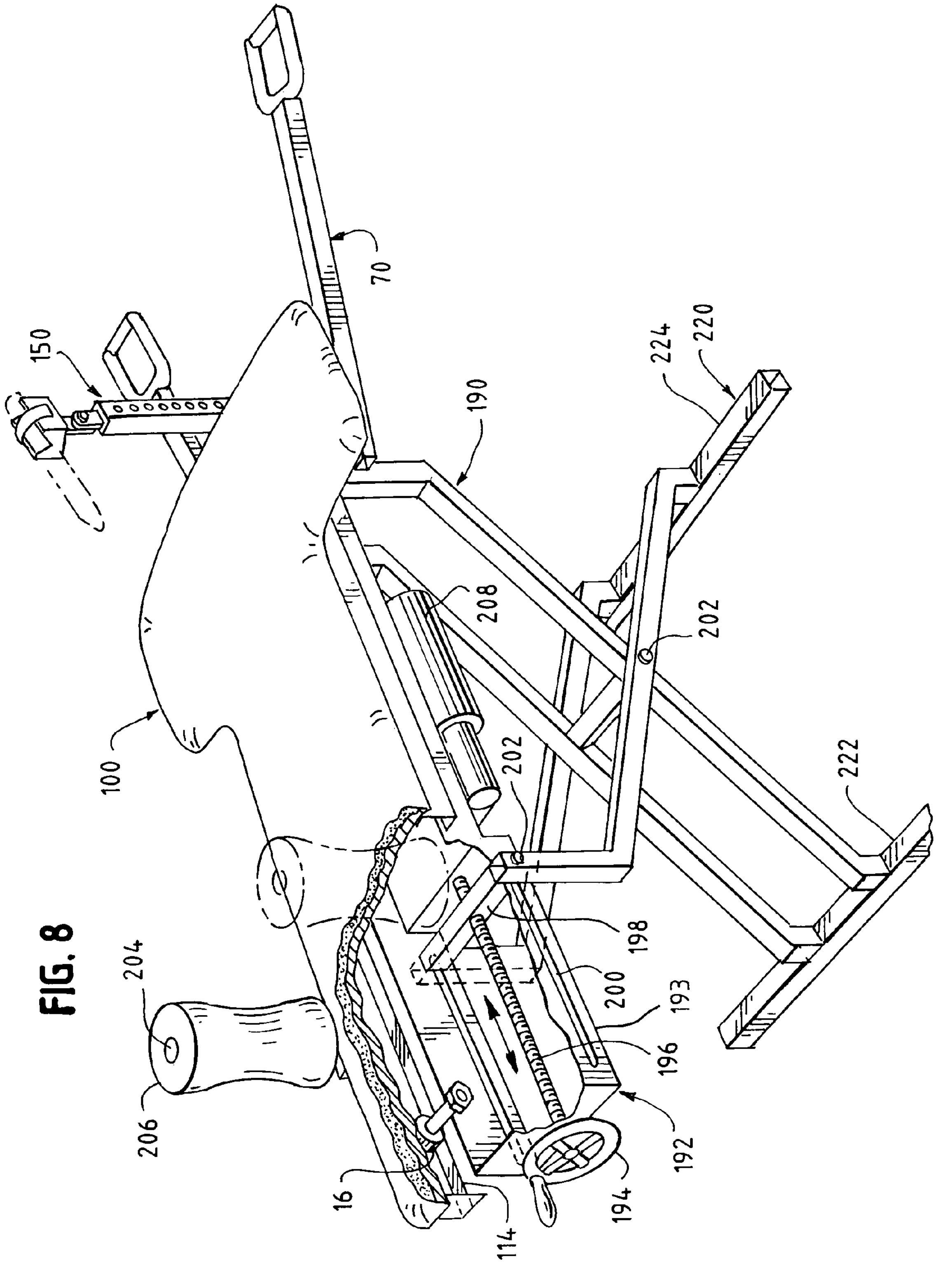
FIG. 8 is a perspective view of the preferred embodiment of the reciprocating sex table machine of this invention.

FIG. 8 shows a preferred embodiment of the sex table. The stirrup assembly 70, the reciprocating platform 100, and the appliance mounting assembly 150 remain substantially unchanged from the previous descriptions. The lower frame is replaced by a fabricated sheet metal pan assembly 192. The fabricated sheet metal pan assembly allows greater design flexibility and facilitates the use of a scissor type height adjustment. The scissor leg assembly 220 consists of a scissor leg inner 222 and a scissor leg outer 224 pivoted in the middle by a bolt 202. An additional bolt 202 attaches the scissor leg outer through a longitudinal slot 200 in the pan 193 and into a threaded tie bar 198. A threaded rod 196 is threaded into the threaded tie bar at one end and affixed to a crank handle 194 at the other end. When the crank handle is turned, the threaded tie bar is pushed or pulled in the longitudinal direction by the rotation of the threaded rod and guided by the longitudinal slots in the pan. This change in the distance between the upper mounting points of the inner and outer legs creates a "scissor" effect. Moving the pivot points further apart will lower the machine height while decreasing that distance will raise the machine height.

Again referring to FIG. 8, the shoulder post 204 and shoulder pad 206 replace the shoulder tube assembly shown in FIG. 1. The shoulder post is welded to the side rails 114 to provide greater rigidity and comfort than the shoulder tube assembly. In addition, the parallel shaft gear motor 30, shown in FIG. 2, is replaced with a right angle gear motor 208 shown in FIG. 8. The right angle gear motor reduces the vertical height of the drive and allows the user to take advantage of the full range of motion of the scissor type height adjustment. The machine can be lowered all the way to the floor for storage and the like, without interference from the gear motor. The functional aspects of the drive are substantially unchanged whether the parallel shaft gear motor, shown in FIG. 2, or the right angle gear motor, shown in FIG. 8, are utilized to power the machine.

I claim:

1. A sex table for use in having sex by one person on the table and a partner having an erect penis beside the sex table, the sex table comprising:

(a) a base containing rollers;

(b) a platform mounted on the rollers of the base, the platform being adapted for supporting the user at a height of about one to three feet; and (c) a means for moving the platform in a linear reciprocating motion relative to the base, wherein the reciprocating motion has a stoke of about one to six inches and a frequency of about 10 to 200 cycles per minute, such that the user can enjoy the reciprocating penetration by the partner's erect penis without the need for the user or the partner to move any part of their bodies.

2. The sex table of claim 1 additionally comprising a means for supporting the legs of the user when the user lies of the platform.

3. The sex table of claim 2 wherein the means for supporting the legs of the user comprises, for each leg, a transverse member having an adjustable distance, a longitudinal member having an adjustable distance, and a stirrup adapted for holding a foot.

4. The sex table of claim 2 additionally comprising a means for changing the height of the platform.

5. The sex table of claim 4 wherein the means for changing the height of the platform comprises a scissors mechanism.

6. The sex table of claim 4 additionally comprising a means for mounting a dildo to the base unit to allow the user to enjoy the reciprocating penetration by the dildo.

7. The sex table of claim 6 wherein the means for mounting a dildo comprises a holder that is adjustable in height and angle.

8. The sex table of claim 6 additionally comprising a means for cushioning and restraining the user.

9. The sex table of claim 8 wherein the means for cushioning and restraining the user comprises vertical tubes attached to the platform.

10. The sex table of claim 8 wherein the platform contains side rails and transverse angle members forming a channel.

11. The sex table of claim 10 wherein the means for moving the platform comprises a motor, an eccentric coupling attached to the motor, the eccentric coupling having an offset bore, and a cam roller mounted in the offset bore of the eccentric coupling means, the cam roller resting in the channel between the transverse angle members of platform.

12. A sex table comprising:

(a) a base containing rollers;

(b) a platform mounted on the rollers of the base, the platform being adapted for supporting a user at a height of about one to three feet, the platform containing side rails and transverse angle members forming a channel; and (c) a motor mounted on the platform, an eccentric coupling attached to the motor, the eccentric coupling having an offset bore, and a cam roller mounted in the offset bore of the eccentric coupling means, the cam roller resting in the channel between the transverse angle members of platform for moving the platform in a linear reciprocating motion relative to the base, wherein the reciprocating motion has a stroke of about one to six inches and a frequency of about 10 to 200 cycles per minute, such that a user can enjoy the reciprocating penetration by a partner's erect penis without the need for the user or partner to move.

13. The sex table of claim 12 additionally comprising a means for supporting the legs of the user when the user lies of the platform, a means for mounting a dildo to the base unit to allow the user to enjoy the reciprocating penetration by the dildo, and a means for cushioning and restraining the user.

14. A method of having sexual intercourse in which a man having an erect penis remains relatively stationary beside a reciprocating sex table upon which a partner rests, the reciprocating motion of the sex table causing a bodily orifice of the sex partner to reciprocate upon the penis, the sex table comprising:

(a) a base containing rollers;

(b) a platform mounted on the rollers of the base, the platform being adapted for supporting a user at a height of about one to three feet; and (c) a means for moving the platform in a linear reciprocating motion relative to the base, wherein the reciprocating motion has a stroke of about one to six inches and a frequency of about 10 to 200 cycles per minute, such that a user can enjoy the reciprocating penetration by a partner's erect penis without the need for the user or partner to move.

15. The method of claim 14 wherein the sex table additionally comprises a means for supporting the legs of the user when the user lies of the platform.

16. The method of claim 15 wherein the sex table additionally comprises a means for changing the height of the platform.

17. The method of claim 16 wherein the sex table additionally comprises a means for mounting a dildo to the base unit to allow the user to enjoy the reciprocating penetration by the dildo.

18. The method of claim 17 wherein the sex table additionally comprises a means for cushioning and restraining the user.

* * * * *